US012329963B2

(12) United States Patent
Lu et al.

(10) Patent No.: US 12,329,963 B2
(45) Date of Patent: Jun. 17, 2025

(54) ANATOMICALLY CONTOURED STIMULATION LEADS FOR HIGH DENSITY NEURAL INTERFACE

(71) Applicant: Verily Life Sciences LLC, South San Francisco, CA (US)

(72) Inventors: Bo Lu, South San Francisco, CA (US); Ken Rys, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 253 days.

(21) Appl. No.: 17/774,397

(22) PCT Filed: Nov. 3, 2020

(86) PCT No.: PCT/US2020/058713
§ 371 (c)(1),
(2) Date: May 4, 2022

(87) PCT Pub. No.: WO2021/091901
PCT Pub. Date: May 14, 2021

(65) Prior Publication Data
US 2022/0387787 A1     Dec. 8, 2022

Related U.S. Application Data

(60) Provisional application No. 62/930,457, filed on Nov. 4, 2019.

(51) Int. Cl.
*A61N 1/05*     (2006.01)
*A61N 1/375*     (2006.01)

(52) U.S. Cl.
CPC ......... *A61N 1/0551* (2013.01); *A61N 1/3752* (2013.01); *A61N 1/0534* (2013.01)

(58) Field of Classification Search
None
See application file for complete search history.

(56) References Cited

U.S. PATENT DOCUMENTS

| 8,886,277 | B2 | 11/2014 | Kim et al. |
| 2004/0257884 | A1* | 12/2004 | Dalton ................. A61N 1/3754 |
| | | | 365/199 |

(Continued)

FOREIGN PATENT DOCUMENTS

| RU | 2286182 | 10/2006 |
| WO | 03092802 | 11/2003 |
| WO | 2018089215 A1 | 5/2018 |

OTHER PUBLICATIONS

Application No. PCT/US2020/058713, International Search Report and Written Opinion, Mailed on Feb. 18, 2021, 7 pages.
(Continued)

*Primary Examiner* — Xiaobei Wang
(74) *Attorney, Agent, or Firm* — Kilpatrick Townsend & Stockton LLP

(57) ABSTRACT

The present disclosure relates to implantable neuromodulation devices and methods of fabrication, and in particular to anatomically contoured spinal cord stimulation leads for high density neural interfaces and methods of microfabricating the stimulation leads. Particularly, aspects are directed to a thin film lead assembly that includes a cable having: a first supporting structure formed of dielectric material, a first set of conductive traces formed on the first supporting structure, a second supporting structure formed of dielectric material, and a second set of conductive traces formed on the second supporting structure. The thin film lead assembly also includes an electrode assembly having: a third supporting structure formed of dielectric material, a first set of electrodes in electrical connection with the first set of conductive traces, and a second set of electrodes in (Continued)

electrical connection with the second set of conductive traces.

16 Claims, 8 Drawing Sheets

(56) References Cited

U.S. PATENT DOCUMENTS

| | | | |
|---|---|---|---|
| 2013/0184799 A1* | 7/2013 | Kipke | A61N 1/0551 607/118 |
| 2015/0157862 A1* | 6/2015 | Greenberg | H05K 3/4061 607/116 |
| 2018/0353753 A1 | 12/2018 | Vetter et al. | |
| 2019/0038438 A1* | 2/2019 | John | A61B 5/24 |
| 2019/0175905 A1 | 6/2019 | Gonzalez et al. | |
| 2019/0336771 A1* | 11/2019 | Voit | A61N 1/36062 |

OTHER PUBLICATIONS

Application No. EP20885258.2, Extended European Search Report, Mailed on Oct. 23, 2023, 7 pages.

\* cited by examiner

ANATOMICALLY CONTOURED STIMULATION LEADS FOR HIGH DENSITY NEURAL INTERFACE

CROSS-REFERENCE TO RELATED APPLICATIONS

This application is a 371 National Phase of International Patent Application No. PCT/US2020/058713, filed Nov. 3, 2020, which claims priority to U.S. Patent Application No. 62/930,457, filed on Nov. 4, 2019, the disclosures of which are incorporated by reference herein in their entireties.

FIELD OF THE INVENTION

The present disclosure relates to implantable neuromodulation devices and methods of fabrication, and in particular to anatomically contoured spinal cord stimulation leads for high density neural interfaces and methods of microfabricating the stimulation leads.

BACKGROUND

Normal neural activity is an intricate balance of electrical and chemical signals which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant containing electronics connected to leads that deliver electrical pulses to electrodes interfaced with nerves or nerve bundles via an electrode assembly. The electrode assembly may be formed of a conductive material and typically take the form of book electrodes, cuff electrodes, spiral cuff electrodes, epidural electrodes, helical electrodes, probe electrodes, linear electrodes, paddle electrodes, and intraneural electrodes.

Conventional electrode assemblies include between four and thirty-two electrodes, and thus typically include four to thirty-two channels or wires connected respectively to the electrodes at the distal end and the electronics of the neurostimulator at the proximal end. However, there is a need for high density neural interfaces that include greater than thirty-two electrodes to interface with larger tissue volumes (e.g., wrapped around the dural sheath of the spinal cord or sub-dural directly on the spinal cord), to recruit smaller populations of neurons for recording, or to provide more targeted therapy by tailoring the electrical stimulation parameters and activated tissue volume. Increasing the density or number of electrodes can increase the number of channels or wires needed to connect the electrodes and the electronics of the neurostimulator. In order to implement high channel or wire counts, there is a need for reliable electrical connections between the electrodes and leads that can maintain contact and electrical isolation in a subject body (e.g., a patient body) for many years. Conventionally, a lead assembly containing a high channel or wire count has the channels or wires connected respectively to the electrodes in a permanent manner. However, these lead assemblies are typically limited in design complexity including channel count and anatomical compliance. Therefore, there is a need for reliable connectors for lead assemblies having high density and anatomically compliant neural interfaces.

BRIEF SUMMARY

In various embodiments, a thin-film lead assembly is provided comprising: a cable comprising: (i) a first supporting structure formed of one or more layers of dielectric material; (ii) a first set of conductive traces formed on a portion of the first supporting structure; (iii) a second supporting structure formed of one or more layers of dielectric material; and (iv) a second set of conductive traces formed on a portion of the second supporting structure; and an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces.

In some embodiments, the first set of electrodes and the second set of electrodes are arranged on the third supporting structure in a honeycomb pattern.

In some embodiments, the first set of electrodes and the second set of electrodes are arranged on the third supporting structure in a plurality of alternating rows comprising a first number of electrodes n and a second number of electrodes n−1.

In some embodiments, the electrode assembly further comprises a proximal end and a distal end, the first supporting structure and the second supporting structure connect with the electrode assembly at the proximal end, and the row of electrodes closest to the first supporting structure and the second supporting structure at the proximal end comprises a third number of electrodes n−2.

In some embodiments, the third supporting structure is thermoset into a cylindrical shape.

In some embodiments, the first set of conductive traces and the second set of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In some embodiments, the one or more layers of dielectric material of the first supporting structure, the second supporting structure, and the third supporting structure are monolithic, and the dielectric material is polyimide, liquid crystal polymer, parylene, polyether ether ketone, or a combination thereof.

In some embodiments, the first supporting structure comprises a proximal end and a distal end, the second supporting structure comprises a proximal end and a distal end, the electrode assembly further comprises a proximal end and a distal end, the distal end of the first supporting structure and the distal end of the second supporting structure are continuous with the proximal end of electrode assembly.

In some embodiments, the thin-film lead assembly further comprises: a first connector formed on the proximal end of the first supporting structure, wherein the first connector comprises a first set of contacts or bond pads in electrical connection with the first set of conductive traces; and a second connector formed on the proximal end of the second supporting structure, wherein the second connector comprises a second set of contacts or bond pads in electrical connection with the second set of conductive traces.

In some embodiments, the first connector is a branched connector comprising: a main body comprising the first supporting structure and the first set of conductive traces; and a plurality of plugs extending from the main body, each plug of the plurality of plugs comprises: an end portion of the first supporting structure comprised of the one or more layers of dielectric material; and a subset of conductive traces from the first set of conductive traces, wherein each trace from the subset of conductive traces terminates at a contact or bond pad of the first set of contacts or bond pads exposed on a surface of the end portion of the first supporting structure.

In some embodiments, the second connector is a branched connector comprising: a main body comprising the second supporting structure and the second set of conductive traces; and a plurality of plugs extending from the main body, each plug of the plurality of plugs comprises: an end portion of the second supporting structure comprised of the one or more layers of dielectric material; and a subset of conductive traces from the second set of conductive traces, wherein each trace from the subset of conductive traces terminates at a contact or bond pad of the second set of contacts or bond pads exposed on a surface of the end portion of the second supporting structure.

In some embodiments, the first supporting structure comprise a first helical portion and the second supporting structure comprises a second helical portion, the first supporting structure and the second supporting structure run in parallel adjacent to one another within the cable.

In some embodiments, the cable further comprises a housing encasing the helical portion of the first supporting structure and the helical portion of the second supporting structure.

In various embodiments, a thin-film lead assembly is provided comprising: a first cable comprising: (i) a first supporting structure formed of one or more layers of dielectric material, and (ii) a first set of conductive traces formed on a portion of the first supporting structure; a second cable comprising: (i) a second supporting structure formed of one or more layers of the dielectric material, and (ii) a second set of conductive traces formed on a portion of the second supporting structure; a first electrode assembly comprising: (i) a backing formed of a polymer material, (ii) a third supporting structure formed of one or more layers of dielectric material, (iii) a first set of electrodes in electrical connection with first set of conductive traces; and a second electrode assembly comprising: (i) the backing formed of the polymer material, (ii) a fourth supporting structure formed of one or more layers of dielectric material, and (iii) a second set of electrodes in electrical connection with the second set of conductive traces.

In some embodiments, the third supporting structure and the fourth supporting structure are formed on the backing, the backing is formed of thermoplastic polyurethane, and the backing, the third supporting structure, and the fourth supporting structure are thermoset into a cylindrical shape.

In some embodiments, the one or more layers of dielectric material of the first supporting structure and the third supporting structure are monolithic, the one or more layers of dielectric material of the second supporting structure and the fourth supporting structure are monolithic, and the dielectric material is polyimide, liquid crystal polymer, parylene, polyether ether ketone, or a combination thereof.

In some embodiments, the first electrode assembly further comprises (iv) a first set of alignment holes formed in the third supporting structure, the second electrode assembly further comprises (iv) a second set of alignment holes formed in the fourth supporting structure, and the first set of alignment holes and the second set of alignment holes are aligned with one another.

In some embodiments, the first supporting structure further comprises a proximal end and a distal end, the second supporting structure further comprises a proximal end and a distal end, the first electrode assembly further comprises a proximal end and a distal end, the second electrode assembly further comprises a proximal end and a distal end, the distal end of the first supporting structure is continuous with the proximal end of the first electrode assembly, and the distal end of the second supporting structure is continuous with the proximal end of the second electrode assembly.

In some embodiments, the thin-film lead assembly further comprises: a first connector formed on the proximal end of the first supporting structure, wherein the first connector comprises a first set of contacts or bond pads in electrical connection with the first set of conductive traces; and a second connector formed on the proximal end of the second supporting structure, wherein the second connector comprises a second set of contacts or bond pads in electrical connection with the second set of conductive traces.

In various embodiments, a neuromodulation system is provided comprising: a neurostimulator comprising an electronics module; a cable comprising: (i) a first supporting structure formed of one or more layers of dielectric material; (ii) a first set of conductive traces formed on a portion of the first supporting structure; (iii) a second supporting structure formed of one or more layers of dielectric material; and (iv) a second set of conductive traces formed on a portion of the second supporting structure; an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces; a first connector formed on a proximal end of the first supporting structure, wherein the first connector comprises a first set of contacts or bond pads in electrical connection with the first set of conductive traces and the electronics module; and a second connector formed on a proximal end of the second supporting structure, wherein the second connector comprises a second set of contacts or bond pads in electrical connection with the second set of conductive traces and the electronics module.

BRIEF DESCRIPTION OF THE DRAWINGS

The present invention will be better understood in view of the following non-limiting figures, in which.

DETAILED DESCRIPTION

I. Introduction

Figure 1:
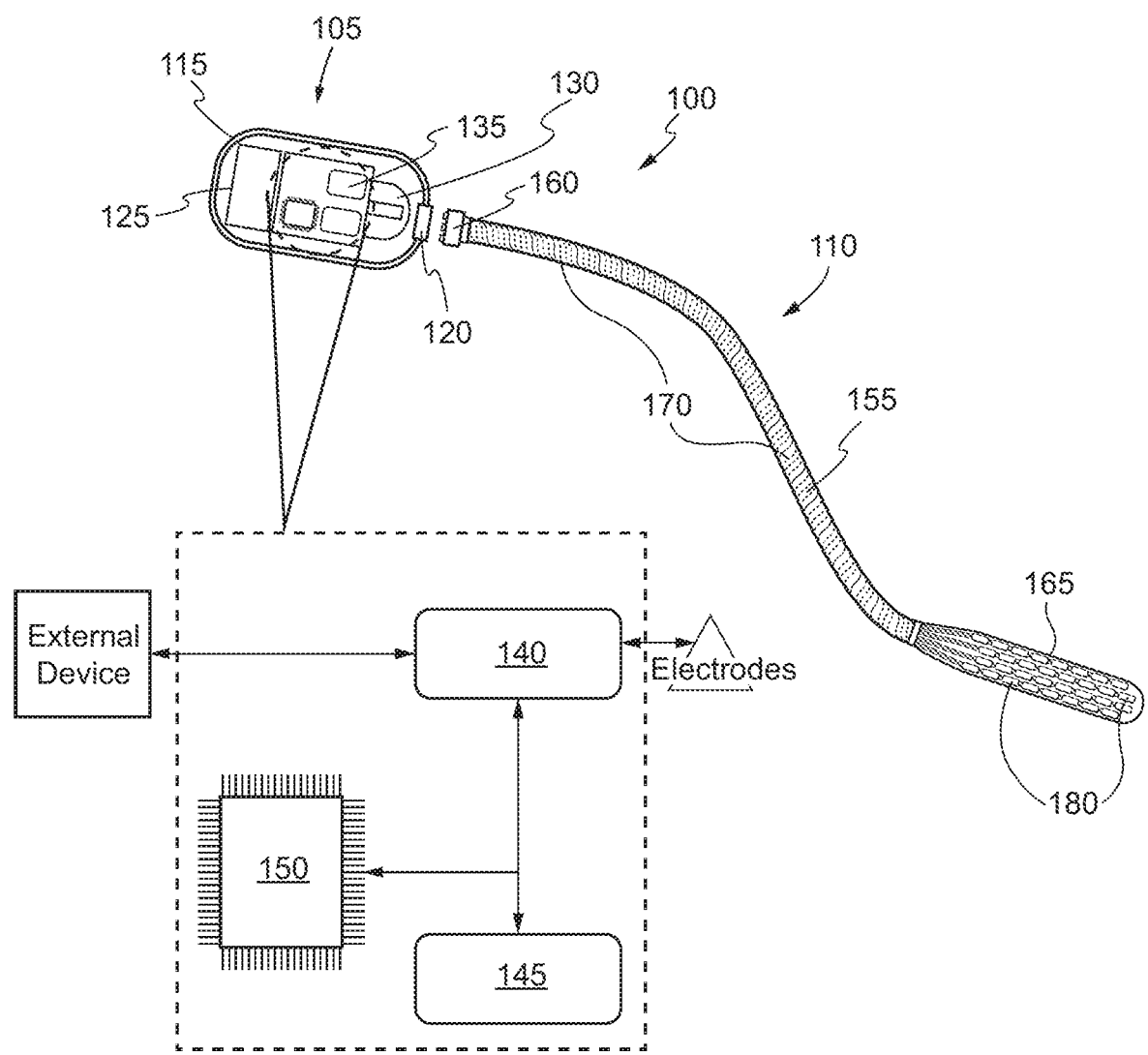
FIG. 1 shows a neuromodulation system in accordance with various embodiments.

The following disclosure describes anatomically contoured spinal cord stimulation leads for high density neural interfaces and methods of microfabricating the stimulation leads. As used herein, the term "proximal" or "proximal end" refers to a first end of the main body, while the term "distal" or "distal end" refers to a second end opposing the first end. For example, the proximal end may be an end of the main body, which is closest to the user, and the distal end may be an end of the main body, which is furthest from the user. The stimulation leads may be fabricated using microfabricating techniques. In certain embodiments, the stimulation leads are fabricated as a monolithic structure. As used herein, the phrase "monolithic" refers to a device fabricated using a same layer of base material. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 µm, or the thickness of a few atoms). Thin films may be deposited by applying a very thin film of material (e.g., between a few nanometers to about 100 µm, or the thickness of a few atoms) onto a substrate surface to be coated, or onto a previously deposited layer of thin film. In various embodiments, a thin film lead assembly is provided comprising a base polymer body (e.g., a supporting structure) and at least one conductive trace formed on the base polymer body. As used herein, the term "high density neural interface(s)" refers to a neural interface that comprises at least thirty-two electrodes (i.e., recording, sensing, stimulating, other types of electrodes, or combinations thereof).

Neuromodulation devices such spinal cord stimulators electrically interface with neural tissue and treat various neurological conditions through electrical stimulation. As described herein, conventional neuromodulation devices comprise a neurostimulator and lead assembly containing between four and thirty-two electrodes. There is a need for high-density lead assemblies that can significantly increase the number of electrodes in order to interface with larger tissue volume, to recruit smaller populations of neurons for recording, or to provide more targeted therapy by tailoring the electrical stimulation parameters and activated tissue volume. Conventional neuromodulation is limited to no more than thirty-two channels per lead assembly due partly to a lack of compatible lead and electrode assembly technology.

To address these limitations and problems, lead assemblies of various embodiments disclosed herein include high density neural interfaces that are capable of being anatomically contoured to a biological system such as a spinal cord. One illustrative embodiment of the present disclosure is directed to a thin film lead assembly comprising: a cable comprising: (i) a first supporting structure formed of one or more layers of dielectric material; (ii) a first set of conductive traces formed on a portion of the first supporting structure; (iii) a second supporting structure formed of one or more layers of dielectric material; and (iv) a second set of conductive traces formed on a portion of the second supporting structure; and an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces.

In other embodiments, a thin film lead assembly is provided that comprises: a first cable comprising: (i) a first supporting structure formed of one or more layers of dielectric material, and (ii) a first set of conductive traces formed on a portion of the first supporting structure; a second cable comprising: (i) a second supporting structure formed of one or more layers of the dielectric material, and (ii) a second set of conductive traces formed on a portion of the second supporting structure; a first electrode assembly comprising: (i) a backing formed of a polymer material, (ii) a third supporting structure formed of one or more layers of dielectric material, (iii) a first set of electrodes in electrical connection with first set of conductive traces; and a second electrode assembly comprising: (i) the backing formed of the polymer material, (ii) a fourth supporting structure formed of one or more layers of dielectric material, and (iii) a second set of electrodes in electrical connection with the second set of conductive traces.

In other embodiments, neuromodulation system comprising: a neurostimulator comprising an electronics module; a cable comprising: (i) a first supporting structure formed of one or more layers of dielectric material; (ii) a first set of conductive traces formed on a portion of the first supporting structure; (iii) a second supporting structure formed of one or more layers of dielectric material; and (iv) a second set of conductive traces formed on a portion of the second supporting structure; an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces; a first connector formed on a proximal end of the first supporting structure, wherein the first connector comprises a first set of contacts or bond pads in electrical connection with the first set of conductive traces and the electronics module; and a second connector formed on a proximal end of the second supporting structure, wherein the second connector comprises a second set of contacts or bond pads in electrical connection with the second set of conductive traces and the electronics module.

Advantageously, these approaches provide a lead assembly, which has increased electrode count (high density neural interface), a smaller footprint, and greater design flexibility. More specifically, these approaches enable lead assemblies with reliable connections between a lead/cable and high density neural interface capable of countering to anatomical biological systems such as the spinal cord. This solution is scalable to connecting many electrodes (e.g., greater than thirty-two) using a single support system or multiple-support systems reflowed on a single backing, and thus enabling several therapeutic opportunities for neurostimulation. Furthermore even for applications where high density neural interfaces are not required, various embodiments can be miniaturized to make the implant minimally invasive, additionally may make invasive anatomies to become accessible (or navigable) due to the miniaturization. It should be understood that although spinal cord neurostimulation and spinal cord device applications are provided as examples of some embodiments, this solution is applicable to all leads and devices that need electrodes/sensors that need to be attached to a neurostimulator.

II. Neuromodulation Devices and Systems with an Electrode Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 may include a housing 115, a feedthrough assembly 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly 120 is attached to a hole in a surface of the housing 115 such that the housing 115 is hermetically sealed. The feedthrough assembly 120 may include one or more feedthroughs (i.e., electrically conductive elements, pins, wires, tabs, pads, etc.) mounted within and extending through the surface of the housing 115 or a cap from an interior to an exterior of the housing 115. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to leads of the lead assembly 110 connected to exterior ends of the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 140 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

The lead assembly 110 may include a lead body 155, a lead connector 160, an electrode assembly 165, and optionally one or more sensors. In some embodiments, the lead connector 160 may be bonding material that bonds conductor material of the lead body 155 to the electronics module 135 of the implantable neurostimulator 105 via the feedthrough assembly 120. The bonding material may be a conductive epoxy or a metallic solder or weld such as platinum. In other embodiments, the lead connector 160 may be conductive wire or tab (e.g., a wire or tab formed of copper, silver, or gold) that bonds conductor material of the lead body 155 to the electronics module 135 of the implantable neurostimulator 105. In alternative embodiments, the implantable neurostimulator 105 and the lead body 155 may be designed to connect with one another via a lead connector 160 such as a branched connector, pin and sleeve connector, snap and lock connector, flexible printed circuit connector, or combination thereof.

The lead body 155 may include one or more leads 170 of conductive material and dielectric material. The one or more leads 170 may carry electrical conductors that allow electrical coupling of the electronics module 135 to electrodes 180 of the electrode assembly 165 via the lead connector 160. In some examples the one or more leads 170 are formed of one or more layers of dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, the dielectric material is polyimide, liquid crystal polymer, parylene, polyether ether ketone, or a combination thereof. The conductive material may be any suitable conductor such as stainless steel, silver, copper or other conductive materials, which may have separate coatings or sheathing for anticorrosive, insulative and/or protective reasons. In certain embodiments, the conductive material copper (Cu), gold (Au), silver (Ag), gold/chromium (Au/Cr), platinum (Pt), platinum/iridium (Pt/Ir), titanium (Ti), gold/titanium (Au/Ti), or any alloy thereof. The conductive material may take various forms including wires, drawn filled tubes, helical coiled conductors, microwires, and/or printed circuits (i.e., conductive traces), for example.

Figure 2:
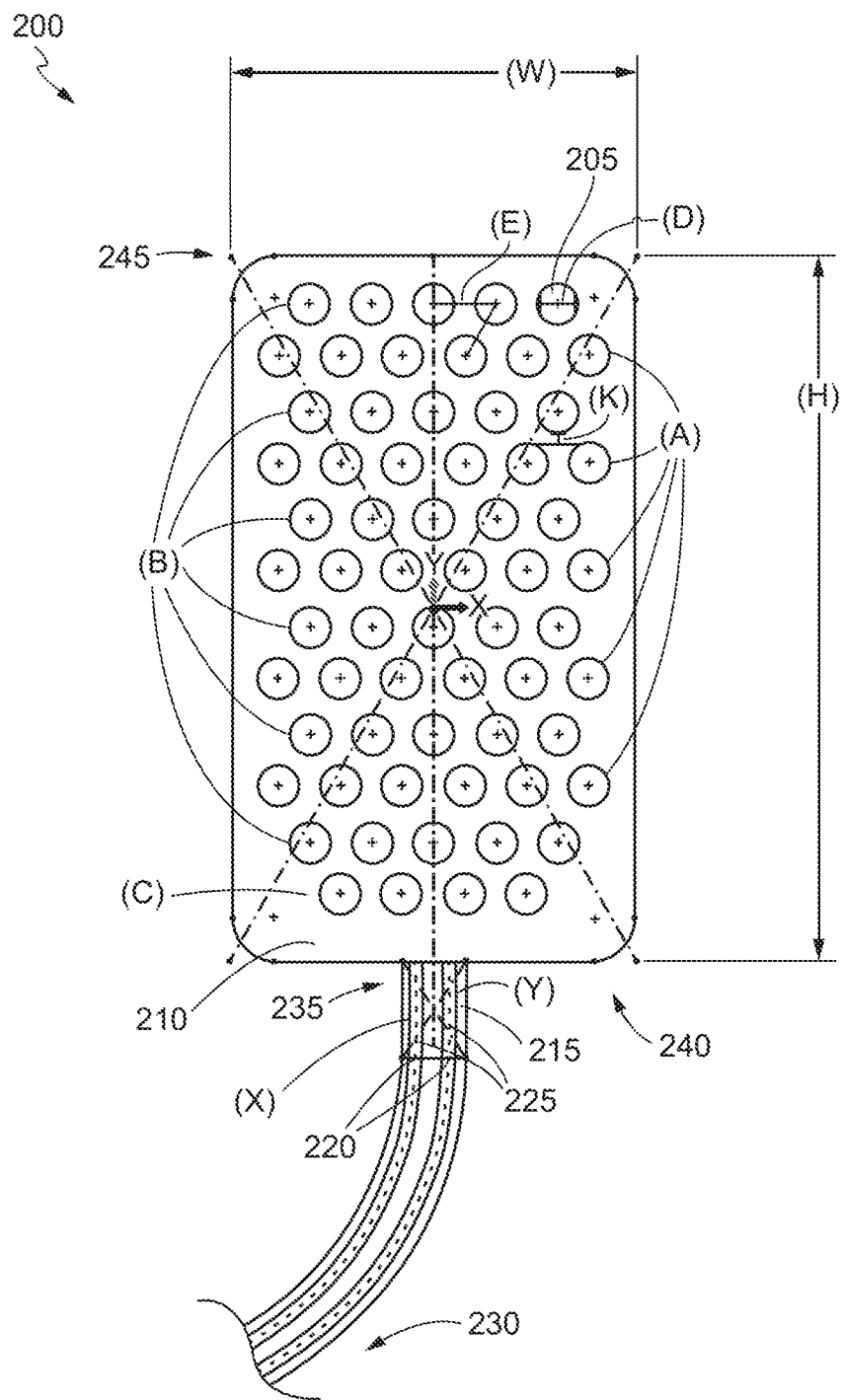
FIG. 2 shows an electrode assembly in accordance with various embodiments.

FIG. 2 shows an electrode assembly 200 in accordance with some aspects of the present invention. In various embodiments, the electrode assembly 200 may include a plurality of electrodes 205 and an supporting structure 210 fabricated in accordance with various aspects. The electrode assembly 200 may be connected to conductor material of a lead body or cable 215 (e.g., a lead body 155 as described with respect to FIG. 1) via one or more leads (e.g., one or more leads 170 as described with respect to FIG. 1). In some embodiments, an end of the cable 215 carries the electrode assembly 200 (e.g., book electrodes, split cuff electrodes, spiral cuff electrodes, epidural electrodes, helical electrodes, probe electrodes, linear electrodes, neural probe, paddle electrodes, and intraneural electrodes). In other embodiments, an end of the cable 215 carries a plurality of electrode assemblies 200.

The supporting structure 210 may be comprised of one or more layers of dielectric material, for example, polyimide, liquid crystal polymer, parylene, polyether ether ketone, or a combination thereof. The one or more layers of dielectric material provide support for microelectronic structures including the plurality of electrodes 205 and a wiring layer (embedded within the one or more dielectric layers). The plurality of electrodes 205 may be electrically connected to the wiring layer via one or more via or contacts, and the wiring layer is used to electrically connect the plurality of electrodes 205 to the one or more leads of the cable 215. The plurality of electrodes 205 and wiring layer may be formed of one or more layers of conductive material. In some instances, the conductive material is copper (Cu), gold (Au), silver (Ag), titanium (Ti), or platinum (Pt), or alloys thereof such as gold/chromium (Au/Cr) or Titanium/Platinum (Ti/Pt), for example. In some embodiments, the plurality of electrodes 205 comprise a top surface that is raised above the top surface of the supporting structure 210 by a predetermined distance. The predetermined distance may be greater than 0.1 µm, greater than 0.5 µm, greater than 1 µm or greater than 10 µm, or the predetermined distance may be from 0.1 µm to 50 µm, from 0.3 µm to 40 µm, from 0.5 µm to 30 µm, or from 1 µm to 25 µm. In other embodiments, the plurality of electrodes 205 comprise a top surface that is coplanar with the top surface of the supporting structure 210. The plurality of electrodes 205 may be formed directly on the supporting structure 210. The term "directly", as used herein, may be defined as being without something in between. Alternatively, the plurality of electrodes 205 may be formed indirectly on the supporting structure 210. The term "indirectly", as used herein, may be defined as having something in between.

The cable 215 may comprise: (i) one or more supporting structures 220 (e.g., one or more leads) formed of one or more layers of dielectric material, for example, polyimide, liquid crystal polymer, parylene, polyether ether ketone, or a combination thereof, and (ii) one or more sets of conductive traces 225 formed on the one or more supporting structures 220 (e.g., one or more leads), respectively. The sets of conductive traces 225 may be comprised of one or more layers of conductive material, and the conductive material may be copper (Cu), gold (Au), silver (Ag), gold/chromium (Au/Cr), platinum (Pt), platinum/iridium (Pt/Ir), titanium (Ti), gold/titanium (Au/Ti), or any alloy thereof. In some instances, the one or more layers of dielectric material of the supporting structure 210 and the one or more layers of dielectric material of the one or more supporting structures 220 are monolithic. More specifically, each of the one or more supporting structures 220 comprises a proximal end 230 and a distal end 235, the electrode assembly 200 further comprises a proximal end 240 and a distal end 245, and the distal end 235 of the one or more supporting structures 220 may be continuous with the proximal end 240 of the electrode assembly 200.

The plurality of electrodes 205 may be separated into two or more sets, e.g., a first set of electrodes (A) and a second set of electrodes (B). The first set of electrodes (A) may be formed on the supporting structure 210 in electrical connection with a first set of conductive traces (X) of the cable 215. The second set of electrodes (B) may be formed on the supporting structure 210 in electrical connection with a second set of conductive traces (Y) of the cable 215. The two or more sets of electrodes (e.g., (A) and (B)) may be arranged on the supporting structure 210 in a predetermined pattern. In some instances, the predetermined pattern is a honeycomb pattern where the first set of electrodes (A) and the second set of electrodes (B) are arranged on the supporting structure 210 in a plurality of alternating rows comprising a first number of electrodes n (e.g., 6) and a second number of electrodes n-1 (e.g., 5). The distal end 235 of the cable 215 connects or is integrated with the proximal end 240 of the electrode assembly 200. In certain instances, a row of electrodes (C) closest to the cable 215 at the proximal end 240 comprises a third number of electrodes n-2 (e.g., 4) to provide more routing flexibility for the wiring layers and conductive traces.

In various embodiments, the supporting structure 210 has a horizontal width (W) and vertical height (H). The horizontal width (W) may range from 5 mm to 50 mm, from 10 mm to 30 mm, from 5 mm to 25 mm, or from 15 mm to 25 mm (for example, 19 mm). The vertical height (h) may range from 5 mm to 90 mm, from 20 mm to 60 mm, from 20 mm to 45 mm, or from 30 mm to 50 mm (for example, 33 mm). Retaining the horizontal width (W) while spacing out the numbers of electrodes n, n-1, and n-2 an equal distance, the supporting structure 210 may be configured to provide a center-to-center spacing (C) for the plurality electrodes 205 that ranges from 0.5 mm to 10 mm, from 0.5 mm to 5 mm, from 1 mm to 8 mm, or from 1 mm to 5 mm (for example, 2.9 mm). The plurality of electrodes 205 may be formed in a predetermined shape on the supporting structure 210. In some instances, the predetermined shape of the plurality of electrodes 205 is a circle having a diameter (D) that ranges from 0.5 mm to 5 mm, from 0.5 mm to 4 mm, from 1 mm to 4 mm, or from 1 mm to 3 mm (for example, 1.9 mm). The plurality of electrodes 205 may have a thickness (T) that ranges from 0.1 µm to 50 µm, from 0.3 µm to 30 µm, from 0.5 µm to 20 µm, or from 1 µm to 15 µm. The plurality of rows of plurality of electrodes 205 may have a spacing (K) that ranges from 0.5 mm to 5 mm, from 0.5 mm to 4 mm, from 1 mm to 4 mm, or from 1 mm to 3 mm (for example, 1.0 mm).

Figure 3A:
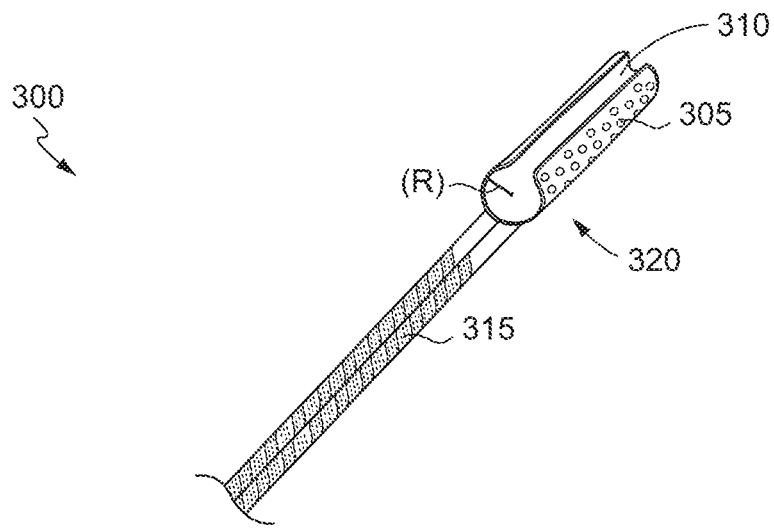
FIGS. 3A, 3B, and 3C show an anatomically contoured electrode assembly in accordance with various embodiments.
Figure 3B:
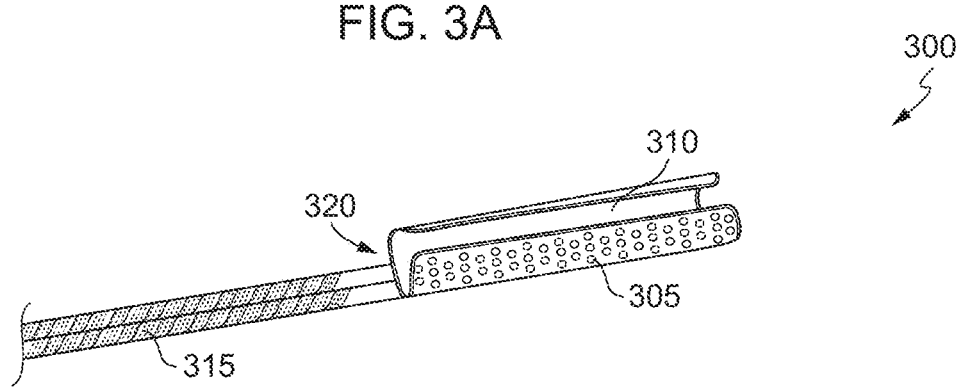
Figure 3C:
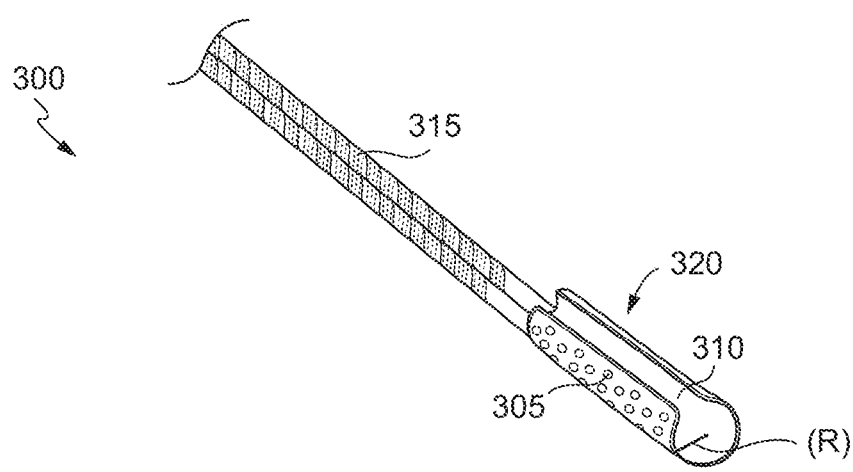

FIGS. 3A-3C show electrode assembly 300 (e.g., the electrode assembly as described with respect to FIG. 2) in accordance with various aspects. In various embodiments, the electrode assembly 300 may include one or more electrodes 305 and a supporting structure 310 fabricated in accordance with various aspects. The electrode assembly 300 may be connected to conductor material of a lead body or cable 315 (e.g., a lead body 155 as described with respect to FIG. 1) via one or more leads (e.g., one or more leads 170 as described with respect to FIG. 1). In some embodiments, the supporting structure 310 may include one or more layers of dielectric material formed in the shape of a structure (e.g., an arc, curl, cylinder, etc.) that allows for the electrode assembly 300 to be opened or closed in order to position the electrode assembly 300 on a nerve or artery/nerve plexus and to allow for the electrode assembly 300 to move with tissue of a patient's body. The one or more layers of dielectric material may also provide support for microelectronic structures including the one or more electrodes 305, wiring layers, and optional vias or contacts. In certain instances, the one or more layers of dielectric material are thermoset with a curled portion 320 having a predetermined radius (R). The radius (R) may be predetermined based on the anatomical structure intended to interface with the electrode assembly 300. For example, the curled portion 320 may have a radius (R) that ranges from 3.5 mm to 7 mm or from 4 mm to 6.5 mm (e.g., 6 mm) to conform with the average human computed tomography spinal cord measurements. In some instances, the radius (R) may be predetermined to fit around the dural sheath between the vertebrae, or could be used sub-dural (beneath the dura, in direct contact with the spinal cord).

Figure 4A:
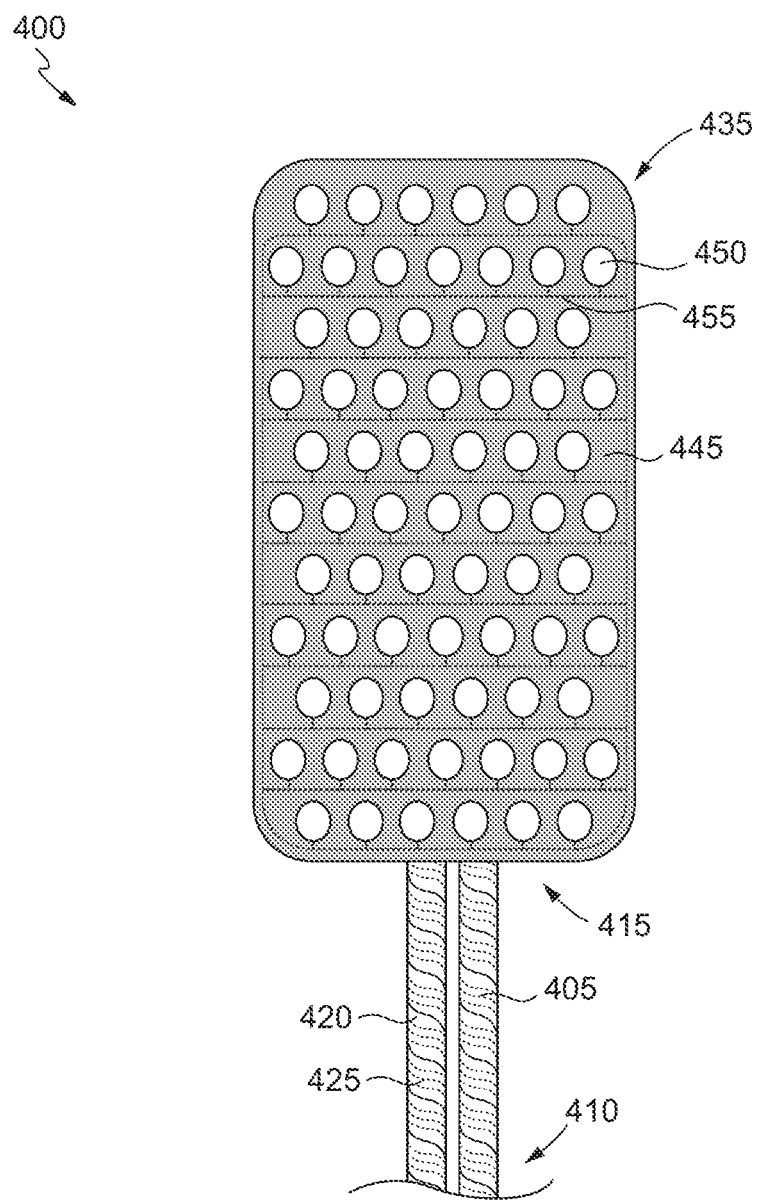
FIGS. 4A and 4B show a lead assembly in accordance with various embodiments.

FIG. 4A shows a lead assembly 400 (e.g., the monolithic lead assembly 110 described with respect to FIG. 1) in accordance with aspects of the present disclosure. In various embodiments, the lead assembly 400 comprises one or more cables 405 having a proximal end 410 and a distal end 415. Each cable 405 may comprise one or more supporting structures 420 and one or more conductive traces 425 formed on a portion of the one or more supporting structures 420. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 420 extends from the proximal end 410 to the distal end 415. In some embodiments, the supporting structure 420 may be made of one or more layers of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 420 may be made of one or more layers of dielectric material formed on a substrate. The substrate may be made from any type of metallic or non-metallic material.

In various embodiments, the supporting structure 420 comprising the one or more layers of dielectric material, and optionally the substrate, has a thickness (G) from the proximal end 410 to the distal end 415. In some embodiments, the thickness (G) is from 10 µm to 150 µm, for example about 50 µm or about 60 µm. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. In some embodiments, the supporting structure 420 has a length (L) of 5 cm to 150 cm or 50 cm to 100 cm, e.g., about 75 cm. In some embodiments, the supporting structure 420 has a width (Z) from a first side horizontally to a second side. In some embodiments, the width (Z) is from 25 µm to 5 mm, for example about 400 µm or about 1000 µm.

In various embodiments, the one or more conductive traces 425 are a plurality of traces, for example, two or more conductive traces or from two to thirty-two conductive traces. The plurality of conductive traces 425 are comprised of one or more layers of conductive material. The conductive material selected for the one or more conductive traces 425 should have good electrical conductivity and may include pure metals, metal alloys, combinations of metals and dielectrics, and the like. For example, the conductive material may be copper (Cu), gold (Au), silver (Ag), gold/chromium (Au/Cr), etc. In some embodiments, it is also desirable that the conductive material selected for the one or more conductive traces 425 have thermal expansion characteristics or a coefficient of thermal expansion (CTE) that is approximately equal to that of CTE of the supporting structure 420. Matching the CTE of components that contact one another is desirable because it eliminates the development of thermal stresses, which may occur during fabrication and the operation of the cable, and thus eliminates a known cause of mechanical failure in the components.

The one or more conductive traces 425 may be deposited onto a surface of the supporting structure 420 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 425 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structure 420. If, however, a signal plane having a relatively low impedance is desired, a greater thickness of electrically conductive material should be deposited onto the supporting structure 420. In certain embodiments, each of the one or more conductive traces 425 has a thickness (J). In some embodiments, the thickness (J) is from 0.5 µm to 100 µm or from 25 µm to 50 µm, for example about 25 µm or about 40 µm. In some embodiments, each of the one or more conductive traces 425 has a length (M) of about 5 cm to 200 cm or 50 cm to 150 cm, e.g., about 80 cm. In certain embodiments, each of the one or more conductive traces 425 extends from the proximal end 410 to the distal end 415. In some embodiments, each of the one or more conductive traces 425 has a width (N) from 2.0 µm to 500 µm, for example about 30 µm or about 50 µm.

Figure 4B:
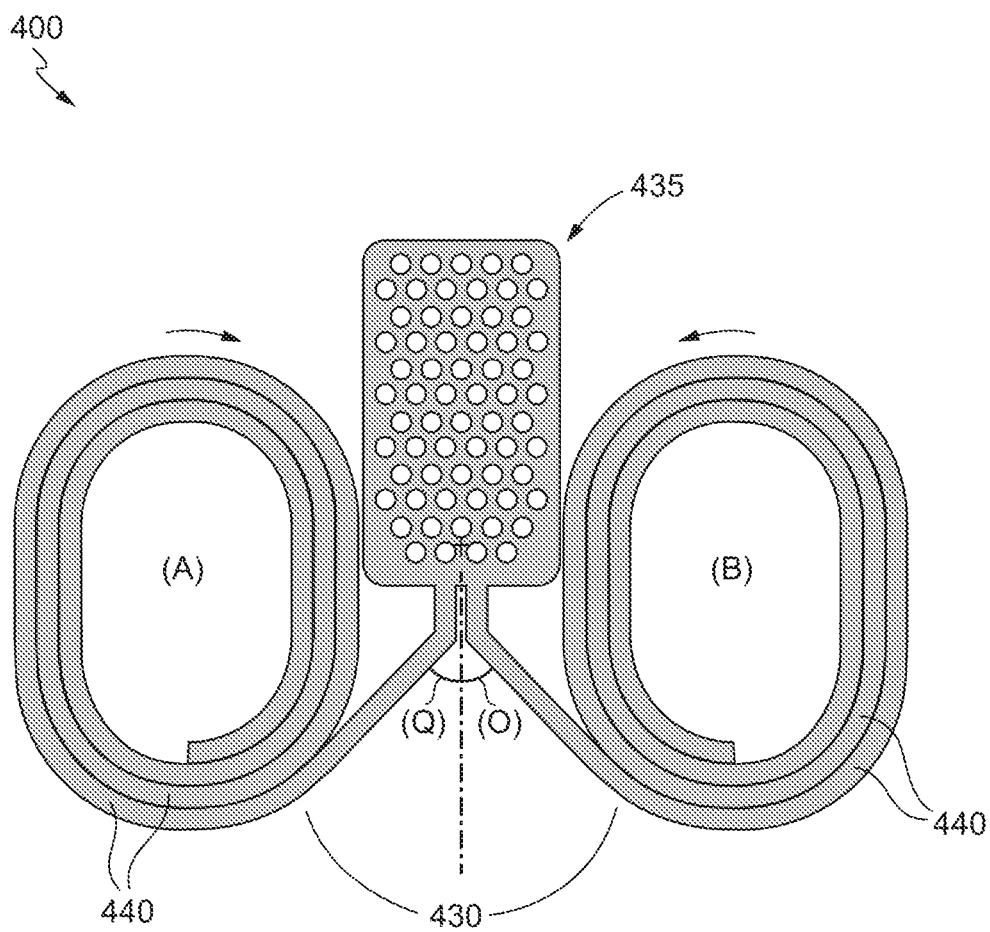

As shown in FIG. 4B, the lead assembly 400 may be formed with a predetermined shape 430 in accordance with aspects of the present disclosure. In particular, the lead assembly 400 may be formed with a predetermined shape 430 from a prefabricated wafer or panel of dielectric material or optionally a substrate. For example, the lead assembly 400 may be laser cut from a prefabricated wafer or panel in one or more spiral shapes 430. The spiral shapes 430 may include characteristics designed to promote a monolithic fabrication process with an electrode assembly 435 and maximize the length of the lead assembly 400 that can be fabricated from a single wafer or panel. Conventionally, wafers or panels have a diameter, length, and/or width of less than 10 cm. In some embodiments, the characteristics of the spiral shapes 430 include a first spiral (A) extending from the electrode assembly 435 at a 40° to 50° angle (Q) (e.g., a 45° angle) and wrapped in a clockwise direction and second spiral (B) extending from the electrode assembly 435 at a 40° to 50° angle (O) (e.g., a 45° angle) and wrapped in a counterclockwise direction to promote a monolithic fabrication process. In some embodiments, the characteristics of the spiral shapes 430 further include a predetermined number of turns 440 and a predetermined pitch (P) between each of the turns 440 to maximize the overall length obtainable for the lead assembly 400. In certain embodiments, the spiral shapes 430 have one or more turns, for example from 2 to 25 turns, and a pitch (P) between each of the turns from 10 µm to 1 cm or from 250 µm to 2 mm, for example about 350 µm. Accordingly, the spiral shapes can maximize the length of the lead assembly 400 that can be fabricated from a single wafer or panel. For example, a single wafer or panel with a limited diameter, length, and/or width of less than 10 cm, can be used to fabricate a lead assembly 400 with a length of 5 cm to 150 cm, 10 cm to 100 cm, or 25 cm to 75 cm, e.g., about 15 cm, using the spiral shapes 430.

With respect back to FIG. 2A, the lead assembly 400 further comprises the electrode assembly 435 comprising a supporting structure 445 that provides support for microelectronic structures including one or more electrodes 450, a wiring layer 455, and optional contact(s) (e.g., the electrode assemblies 200 and 300 as described with respect to FIGS. 2, 3A, 3B, and 3C). The electrode assembly 435 may be located at the distal end 415 of the lead assembly 400. In various embodiments, the supporting structure 445 of the lead assembly and the supporting structure 420 of the one or more cables 405 are the same structure (i.e., the supporting structure is continuous from the proximal end 410 to the distal end 415), which thus creates a monolithic lead assembly 400. In some embodiments, the supporting structure 445 for the electrode assembly 435 comprises the one or more layers of dielectric material, and optionally the substrate, and has a thickness (V) of from 10 µm to 150 µm, from 15 µm to 70 µm, from 30 µm to 60 µm, or from 40 µm to 60 µm.

The wiring layer 455 may be formed on the supporting structure 445. In various embodiments, the wiring layer 455 is formed continuously of the one or more conductive traces 425, and is comprised of various metals or alloys thereof, for example, copper (Cu), gold (Au), silver (Ag), gold/chromium (Au/Cr), platinum (Pt), platinum/iridium (Pt/Ir), titanium (Ti), gold/titanium (Au/Ti), or any alloy thereof. The wiring layer 455 may have a thickness (E) of from 0.5 µm to 100 µm, from 0.5 µm to 15 µm, from 0.5 µm to 10 µm, or from 0.5 µm to 5 µm. In some embodiments, a top surface of the wiring layer 455 is coplanar with a top surface of the supporting structure 445. In other embodiments, the wiring layer 455 is embedded within the supporting structure 445. In yet other embodiments, the wiring layer 455 is formed on the top surface of the supporting structure 445 and the top surface of the wiring layer 455 is raised above the top surface of the supporting structure 445.

In some embodiments, the one or more electrodes 450 are formed on the supporting structure 445 and in electrical contact with the wiring layer 455. The one or more electrodes 450 may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example. The one or more electrodes 450 may be formed directly on the supporting structure 445. Alternatively, the one or more electrodes 450 may be formed indirectly on the supporting structure 445. In some embodiments, the contact(s) are formed on the supporting structure 445 and provide electrical contact between the one or more electrodes 450 and the wiring layer 455. The contact(s) may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example.

The properties of the supporting structures and electronic structures (e.g., thickness, material, position, contact, etc.) of the lead assembly 400 may be the same or different from those of the structures previously discussed herein with reference to FIGS. 2, 3A, 3B, and 3C. However, it should be understood the lead assembly 400 is an exemplary embodiment, and that the lead assembly 400 is to be construed with the broadest sense to include variations of the specific design and/or performance need described herein, as well as other variations that are well known to those of skill in the art. In particular, the shape and location of components and layers in the lead assembly 400 may be adjusted or modified to meet specific design and/or performance needs. Furthermore, it is to be understood that other structures may have been omitted from the description of the lead assembly 400 for clarity. The omitted structures may include, for example, sensor structures, insulating layers, interconnect components, passive devices, etc.

Figure 5A:
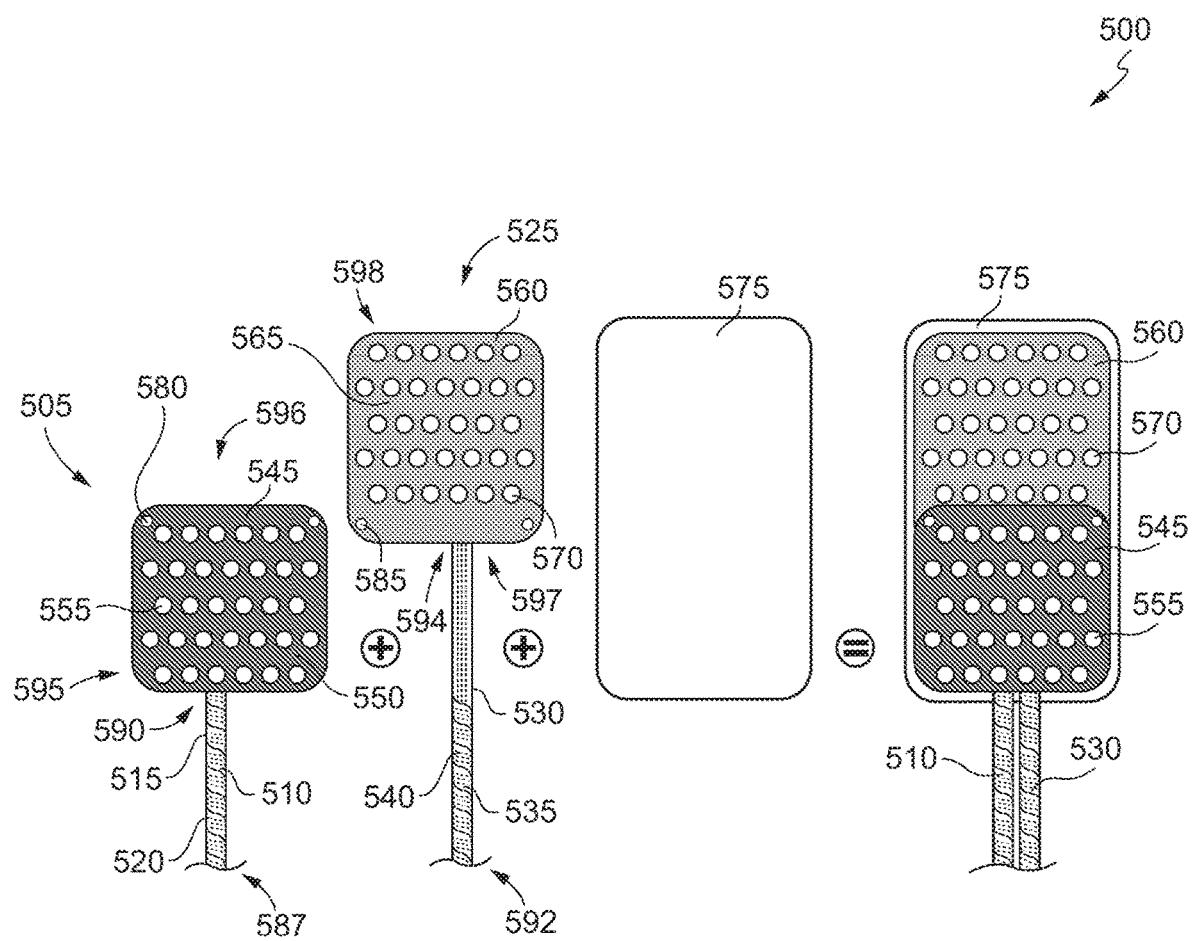
FIGS. 5A, 5B, 5C, and 5D show an alternative electrode assembly in accordance with some aspects of the present invention.

FIG. 5A shows an alternative lead assembly 500 (e.g., the monolithic lead assembly 110 described with respect to FIG. 1) in accordance with aspects of the present disclosure. In various embodiments, the supporting structures and electronic structures described with respect to FIGS. 2, 3A, 3B, 3C, 4A, and 4B can be arranged into separate subpanels that are then stacked together and stitched into a single structure using a backing. For example, a first subpanel 505 may be provided that comprises a first cable 510 comprising: (i) a first supporting structure 515 formed of one or more layers of dielectric material, and (ii) a first set of conductive traces 520 formed on a portion of the first supporting structure 515. A second subpanel 525 may be provided that comprises a second cable 530 comprising: (i) a second supporting structure 535 formed of one or more layers of dielectric material, and (ii) a second set of conductive traces 540 formed on a portion of the second supporting structure 535. The first subpanel 505 may further comprise a first electrode assembly 545 comprising: (i) a third supporting structure 550 formed of one or more layers of dielectric material, and (ii) a first set of electrodes 555 in electrical connection with first set of conductive traces 520. The second subpanel 525 may further comprise a second electrode assembly 560 comprising: (i) a fourth supporting structure 565 formed of one or more layers of dielectric material, and (ii) a second set of electrodes 570 in electrical connection with second set of conductive traces 540.

Figure 5B:
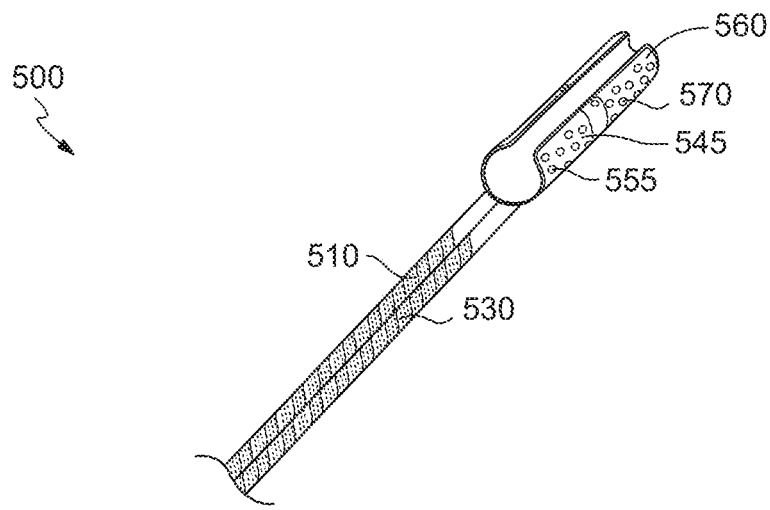
Figure 5C:
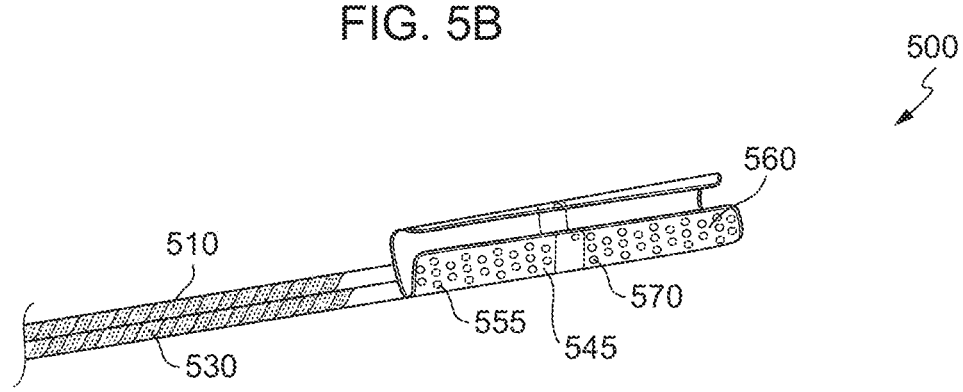
Figure 5D:
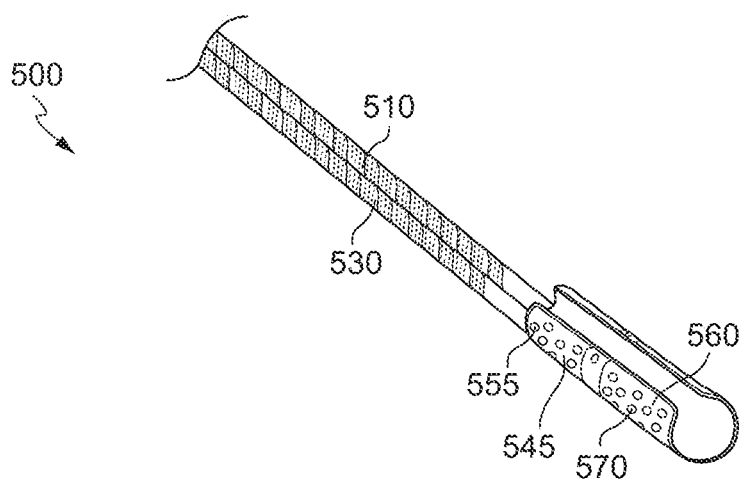

In various embodiments, the third supporting structure 550 and the fourth supporting structure 565 are formed on a backing 575 to fabricate the final structure of the alternative lead assembly 500. In some instance, the backing is formed of thermoplastic polyurethane, and the backing, the third supporting structure, and the fourth supporting structure are thermoset into a cylindrical shape, as shown in FIGS. 5B, 5C, and 5D. In some embodiments, the first electrode assembly 545 further comprises (iv) a first set of alignment holes 580 formed in the third supporting structure 550, the second electrode assembly 560 further comprises (iv) a second set of alignment holes 585 formed in the fourth supporting structure 565, and the first set of alignment holes 580 and the second set of alignment holes 585 are aligned with one another to assist in fabrication and attachment o backing 575.

The one or more layers of dielectric material of the first supporting structure 515 and the third supporting structure 550 may be monolithic, the one or more layers of dielectric material of the second supporting structure 540 and the fourth supporting structure 565 may be monolithic, and the dielectric material is polyimide, liquid crystal polymer, parylene, polyether ether ketone, or a combination thereof. The first supporting structure 515 further comprises a proximal end 587 and a distal end 590, the second supporting structure 535 further comprises a proximal end 592 and a distal end 594, the first electrode assembly 545 further comprises a proximal end 595 and a distal end 596, the second electrode assembly 560 further comprises a proximal end 597 and a distal end 598, the distal end 590 of the first supporting structure 515 is continuous with the proximal end 595 of the first electrode assembly 545, and the distal end 594 of the second supporting structure 535 is continuous with the proximal end 597 of the second electrode assembly 560. It should be understood that although only two subpanels are discussed with respect to lead assembly 500, the use of any number and combination of subpanels is contemplated and applicable to all leads and devices that need electrodes/sensors that need to be attached to a neurostimulator.

Figure 6:
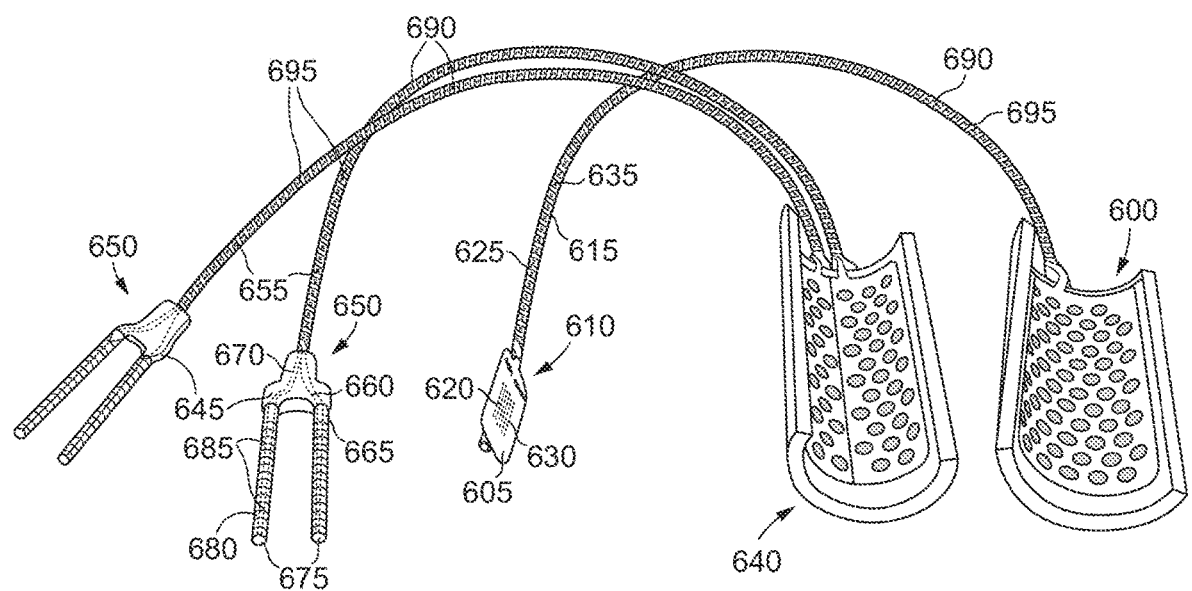
FIG. 6 shows electrode assemblies in accordance with some aspects of the present invention.

FIG. 6 shows that a lead assembly may further comprise connector (e.g., connector 120 described with respect to FIG. 1). In some instances, a lead assembly 600 (e.g., lead assembly 400 described with respect to FIGS. 4A and 4B) may comprise a single connector body 605 formed on the proximal end 610 of a cable 615. The single connector body 605 may comprise a first set of contacts or bond pads 620 in electrical connection with a first set of conductive traces 625 and a second set of contacts or bond pads 630 in electrical connection with a second set of conductive traces 635. Alternatively (not shown), a lead assembly 600 (e.g., lead assembly 400 described with respect to FIGS. 4A and 4B) may comprise multiple connector bodies formed on the proximal end 610 of a cable 615. Each connector bodies may comprise a set of contacts or bond pads in electrical connection with a set of conductive traces. Alternatively (not shown), a lead assembly 600 (e.g., lead assembly 400 described with respect to FIGS. 4A and 4B) may comprise multi-branched connector (see for example branched connector 645) formed on the proximal end 610 of a cable 615. Each branch or plug of the multi-branched connector may comprise a set of contacts or bond pads in electrical connection with a set of conductive traces.

In some instances, a lead assembly 640 (e.g., lead assembly 500 described with respect to FIGS. 5A, 5B, 5C, and 5D) may comprise multiple connector bodies 645 formed on the proximal ends 650 of multiple cables 655. Each connector body 645 may comprise a main body 660 comprising a supporting structure 665 and a set of conductive traces 670, and a plurality of branches or plugs 675 extending from the main body 660. Each plug of the plurality of plugs 675 comprises: an end portion of the supporting structure 665 comprised of the one or more layers of dielectric material and a subset of conductive traces 680 from the set of conductive traces 670. Each trace from the subset of conductive traces 680 terminates at a contact or bond pad 685 exposed on a surface of the end portion of the supporting structure 665. Alternatively (not shown), a lead assembly 640 (e.g., lead assembly 400 described with respect to FIGS. 4A and 4B) may comprise one or more connector bodies (for example see connector 605) formed on the proximal ends 650 of cables 655. Each connector bodies may comprise a set of contacts or bond pads in electrical connection with a set of conductive traces.

FIG. 6 further shows the supporting structures of the cable 615 may have one or more helical portions 690. The supporting structures of the cable 615 may be arranged to run in parallel adjacent to one another within the cable 615. In some instances, the cable 615 further comprises a housing 695 encasing the helical portions 690 of the supporting structures. Moreover, the supporting structures of the cables 655 may have one or more helical portions 690. In some instances, the cables 655 further comprise a housing 695 encasing the helical portions 690 of the supporting structures.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A thin-film lead assembly comprising:
   a cable comprising: (i) a first supporting structure formed of one or more layers of dielectric material, (ii) a first set of conductive traces formed on a portion of the first supporting structure, (iii) a second supporting structure formed of one or more layers of dielectric material, and (iv) a second set of conductive traces formed on a portion of the second supporting structure;
   an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces; and
   a connector comprising: (i) a fourth supporting structure formed on an end of the first supporting structure and an end of the second supporting structure, (ii) a first set of contacts or bond pads formed on at least a portion of the fourth supporting structure in electrical connection with the first set of conductive traces, and (iii) a second set of contacts or bond pads on at least another portion of the fourth supporting structure in electrical connection with the second set of conductive traces,
   wherein the one or more layers of dielectric material of the first supporting structure, the second supporting structure, and the third supporting structure are monolithic, and the dielectric material is polyimide, liquid crystal polymer, parylene, polyether ether ketone, or a combination thereof.

2. The thin-film lead assembly of claim 1, wherein the first set of electrodes and the second set of electrodes are arranged on the third supporting structure in a honeycomb pattern.

3. The thin-film lead assembly of claim 2, wherein the first set of electrodes and the second set of electrodes are arranged on the third supporting structure in a plurality of alternating rows comprising a first number of electrodes n and a second number of electrodes n−1.

4. The thin-film lead assembly of claim 3, wherein the electrode assembly further comprises a proximal end and a distal end, the first supporting structure and the second supporting structure connect with the electrode assembly at the proximal end, and a row of electrodes closest to the first supporting structure and the second supporting structure at the proximal end comprises a third number of electrodes n−2.

5. The thin-film lead assembly of claim 1, wherein the third supporting structure is thermoset into a cylindrical shape.

6. The thin-film lead assembly of claim 1, wherein the first set of conductive traces and the second set of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

7. The thin-film lead assembly of claim 1, wherein the first supporting structure comprises a proximal end and a distal end, the second supporting structure comprises a proximal end and a distal end, the electrode assembly further comprises a proximal end and a distal end, the distal end of the first supporting structure and the distal end of the second supporting structure are continuous with the proximal end of the electrode assembly.

8. The thin-film lead assembly of claim 1, wherein:
the connector is a branched connector comprising:
a first plug extending from the at least the portion of the fourth supporting structure, and
a second plug extending from the at least the another portion of the fourth supporting structure.

9. The thin-film lead assembly of claim 1, wherein the first supporting structure comprises a first helical portion and the second supporting structure comprises a second helical portion, the first supporting structure and the second supporting structure run in parallel adjacent to one another within the cable.

10. The thin-film lead assembly of claim 9, wherein the cable further comprises a housing encasing the first helical portion of the first supporting structure and the second helical portion of the second supporting structure.

11. A thin-film lead assembly comprising:
a first cable comprising: (i) a first supporting structure formed of one or more layers of dielectric material, and (ii) a first set of conductive traces formed on a portion of the first supporting structure;
a second cable comprising: (i) a second supporting structure formed of one or more layers of the dielectric material, and (ii) a second set of conductive traces formed on a portion of the second supporting structure;
a first electrode assembly comprising: (i) a third supporting structure formed of one or more layers of dielectric material, and (ii) a first set of electrodes in electrical connection with first set of conductive traces;
a second electrode assembly comprising: (i) a fourth supporting structure formed of one or more layers of dielectric material, and (ii) a second set of electrodes in electrical connection with the second set of conductive traces, wherein the first electrode assembly and the second electrode assembly are disposed on a backing formed of a polymer material;
a first connector comprising: (i) a fifth supporting structure formed on an end of the first supporting structure, (ii) a first set of contacts or bond pads formed on at least a portion of the fifth supporting structure in electrical connection with the first set of conductive traces, and (iii) a second set of contacts or bond pads on at least another portion of the fifth supporting structure in electrical connection with the first set of conductive traces; and
a second connector comprising: (i) a sixth supporting structure formed on an end of the second supporting structure, (ii) a third set of contacts or bond pads formed on at least a portion of the sixth supporting structure in electrical connection with the second set of conductive traces, and (iii) a fourth set of contacts or bond pads on at least another portion of the sixth supporting structure in electrical connection with the second set of conductive traces.

12. The thin-film lead assembly of claim 11, wherein the third supporting structure and the fourth supporting structure are formed on the backing, the backing is formed of thermoplastic polyurethane, and the backing, the third supporting structure, and the fourth supporting structure are thermoset into a cylindrical shape.

13. The thin-film lead assembly of claim 12, wherein the one or more layers of dielectric material of the first supporting structure and the third supporting structure are monolithic, the one or more layers of dielectric material of the second supporting structure and the fourth supporting structure are monolithic, and the dielectric material is polyimide, liquid crystal polymer, parylene, polyether ether ketone, or a combination thereof.

14. The thin-film lead assembly of claim 12, wherein the first electrode assembly further comprises (iv) a first set of alignment holes formed in the third supporting structure, the second electrode assembly further comprises (iv) a second set of alignment holes formed in the fourth supporting structure, and the first set of alignment holes and the second set of alignment holes overlap with one another.

15. The thin-film lead assembly of claim 11, wherein the first supporting structure further comprises a proximal end and a distal end, the second supporting structure further comprises a proximal end and a distal end, the first electrode assembly further comprises a proximal end and a distal end, the second electrode assembly further comprises a proximal end and a distal end, the distal end of the first supporting structure is continuous with the proximal end of the first electrode assembly, and the distal end of the second supporting structure is continuous with the proximal end of the second electrode assembly.

16. A neuromodulation system comprising:
a neurostimulator comprising an electronics module;
a cable comprising:
(i) a first supporting structure formed of one or more layers of dielectric material;
(ii) a first set of conductive traces formed on a portion of the first supporting structure;
(iii) a second supporting structure formed of one or more layers of dielectric material; and
(iv) a second set of conductive traces formed on a portion of the second supporting structure;
an electrode assembly comprising: (i) a third supporting structure formed of one or more layers of dielectric material, (ii) a first set of electrodes in electrical connection with the first set of conductive traces, and (iii) a second set of electrodes in electrical connection with the second set of conductive traces;
a first connector formed on a proximal end of the first supporting structure, wherein the first connector comprises a first set of contacts or bond pads in electrical connection with the first set of conductive traces and the electronics module; and
a second connector formed on a proximal end of the second supporting structure, wherein the second connector comprises a second set of contacts or bond pads in electrical connection with the second set of conductive traces and the electronics module,
wherein the one or more layers of dielectric material of the first supporting structure, the second supporting structure, and the third supporting structure are monolithic, and the dielectric material is polyimide, liquid crystal polymer, parylene, polyether ether ketone, or a combination thereof.

* * * * *